United States Patent [19]

Fischetti et al.

[11] Patent Number: 5,643,767
[45] Date of Patent: Jul. 1, 1997

[54] PROCESS FOR ISOLATING CELLULAR COMPONENTS

[75] Inventors: Vincent A. Fischetti, West Hempstead; Ambrose Cheung, New York, both of N.Y.

[73] Assignee: The Rockefeller University, New York, N.Y.

[21] Appl. No.: 412,388

[22] Filed: Mar. 28, 1995

Related U.S. Application Data

[63] Continuation-in-part of Ser. No. 236,536, May 2, 1994, abandoned, and Ser. No. 236,537, May 2, 1994, abandoned.

[51] Int. Cl.$^6$ .............................. C07H 1/00; C07H 21/00
[52] U.S. Cl. .................... 435/91.3; 435/91.1; 536/25.41; 935/19; 935/20
[58] Field of Search ................. 536/25.4, 25.41, 536/25.42; 435/91.1, 91.3; 935/19, 20

[56] References Cited

U.S. PATENT DOCUMENTS

| | | | |
|---|---|---|---|
| 4,843,155 | 6/1989 | Chomczynski | 536/25.42 |
| 5,010,183 | 4/1991 | MacFarlane | 536/25.4 |
| 5,374,522 | 12/1994 | Murphy et al. | 435/6 |

OTHER PUBLICATIONS

Dana et al., 1995, J. NIH Res. 7:63.
Lunsford, 1995, Biotechniques 18:412-13.
Cheung et al., 1995, 94th ASM General Meeting, Session 176, p. 227 (abs. H-154).
Triesenberg, 1994, "Primer Extension", *Current Protocols in Molecular Biology*, F.M. Ausubel et al. (eds.), Wiley, New York, pp. 4.8.1-4.8.5.
Chomczynski, 1993, Biotechniques 15:532-36.
Kinger et al., 1993, Biotechniques 14:724-25.
Bradshaw and Pillar, 1992, J. Microbiological Meth. 15:1-5.
Chomczynski, 1992, Anal. Biochem. 201:134-39.
Chomczynski, 1992, Nucl. Acids Res. 20:3791-92.
Santos et al., 1992, J. Microbiological Meth. 15:83-94.
Patel et al., 1991, J. Microbiol. Meth. 13:99-111.
Reddy and Gilman, 1991, "Preparation of bacterial RNA", *Current Protocols in Molecular Biology*, F.M. Ausubel et al. (eds.), Wiley, New York, pp. 4.4.1-4.4.7.
Rymaszewski et al., 1990, Anal. Biochem. 188:91-96.
Kornblum et al., 1988, Gene 63:75-85.
Sandler and Weisblum, 1988, J. Mol. Biol. 203:905-915.
Chomczynski and Sacchi, 1987, Anal. Biochem. 162:156-59.
Katoch and Cox, 1986, Int'l J. leprosy 54:409-14.
Nossal, 1953, Austral. J. exp. Biol. 31:583-90.

*Primary Examiner*—Gary L. Kunz
*Attorney, Agent, or Firm*—Klauber & Jackson

[57] ABSTRACT

A reagent, method and container for the isolation of cellular components such as ribonucleic acid (RNA) from cells in a liquid solution. The container includes a cover assembly and a holder which is normally closed by the cover assembly and contains an RNA extractant solvent, micron-sized particles and at least one larger particle suitably of millimeter size. The container contains the reagent, which is an extractant solvent which contains phenol and guanidinium thiocyanate or guanidinium chloride and has a pH of about 4. The container also includes a friable sealing layer which separates the extractant solvent from the liquid medium containing the cells until the container is reciprocally shaken. The method includes the reciprocal shaking of the container, wherein the larger particle breaks the friable layer to permit mixing of the liquid medium with the extractant solvent resulting in the breaking of the cell walls by the micron-size beads and the release of the RNA.

10 Claims, 5 Drawing Sheets

PROCESS FOR ISOLATING CELLULAR COMPONENTS

CROSS-REFERENCE TO RELATED APPLICATIONS

This application is a continuation-in-part of U.S. patent application Ser. Nos. 08/236,536 and 08/236,537, filed May 2, 1994, both now abandoned, which are based in part on U.S. patent application Ser. Nos. 08/227,514 and 08/227,516, filed Apr. 14, 1994, both now abandoned. These applications are hereby incorporated by reference in their entirety.

BACKGROUND OF THE INVENTION

1. Field of the Invention

This invention relates to reagents, methods and apparatus for the isolation of cellular components such as ribonucleic acid (RNA) from natural cellular sources.

2. Description of the Related Art

Cells contain a wide variety of cellular components appropriate to their function. They contain, for example, DNA, ribonucleic acid (RNA) and their expression products including a host of proteinaceous materials. This invention is useful for the isolation of such cellular components, but for convenience, the invention will be described principally as it applies to the isolation of RNA.

RNA is a critical component in the sequence of biological reactions which results in the expression of the myriads of proteins including hormones, enzymes and structural tissue essential for the existence of all forms of life. There is a critical need for large amounts of RNA for research purposes as well as diagnostic and therapeutic uses.

Plant cells and microorganisms including parasites, yeast and, bacteria, are potential sources of RNA, but because the cell walls of RNA sources are so strong, it is difficult, time consuming and may require expensive equipment to utilize them as RNA sources.

RNA isolation from bacteria is difficult because the cell walls are not readily susceptible to lysis. Current protocols for isolating RNA from bacteria frequently employ enzymes such as lysostaphin or lysozyme to lyse the bacterial cells followed by the addition of denaturing agents to inactivate the ribonucleases. However, these methods have not proven to be useful for the isolation of large amounts of high purity RNA.

U.S. Pat. No. 4,843,155 employs an RNA isolation procedure in which biological tissue such as mouse anterior pituitaries are initially homogenized in a "glass-teflon homogenizer" in an aqueous buffered medium at pH 4 containing phenol, a guanidinium salt such as guanidinium thiocyanate and, possibly an antioxidant. The homogenate is then extracted with an organic solvent insoluble in the buffer. Chloroform is exemplified as a useful solvent. The RNA remains dissolved in the aqueous buffer. The DNA and protein of the biological tissue concentrate at the interface between the organic and inorganic phases. The RNA is separated from the aqueous phase by precipitation with a water soluble alkanol such as isopropanol. The RNA may be recovered by centrifugation and removing of the supernatant. The patentee states that the isolation procedure can be completed in three hours.

This procedure is inconvenient because guanidine salts are expensive and malodorous. Moreover, as described, the method is limited to biological tissue (i.e., eukaryotic and not prokaryotic cells) as an RNA source and requires an extended period of time to complete. The cells in biological tissue, being eukaryotic, are enclosed by a fragile membrane which is easily ruptured.

Moreover, although glass beads have been used in methods of RNA isolation, glass beads cannot be used in conjunction with a homogenizer-type apparatus to achieve the results of the present invention, because beads would cause the homogenizer to jam. Glass beads have been used in conjunction with a bead beater to isolate nucleic acids from cells. However, the disadvantage to this method lies in the fact that the method smashes the cells, releasing the contents into medium in which unstable cellular components, such as RNA, are rapidly degraded by enzymes that are released.

Therefore, in view of the aforementioned deficiencies attendant with prior art methods of isolating cellular components such as RNA from cells, it should be apparent that there still exists a need in the art for reagents, methods and apparati suitable for the efficient isolation of such components from both eukaryotic and prokaryotic cells.

SUMMARY AND OBJECTS OF THE INVENTION

Accordingly, a major object of the present invention is to provide a method of isolating a cellular component including mechanically releasing such component by the application of reciprocal mechanical energy to a suspension of cells in a liquid medium in a container which also contains a plurality of micron-size particles thereby to fracture the cell walls and release the cell component into the liquid medium and isolating the selected cell component from the medium.

Another object of the present invention is to provide a method of isolating RNA from a cellular source containing it together with DNA and protein including the steps of:

a. mechanically releasing the RNA from a cellular source containing it by the application of reciprocal energy in the presence of an extraction solvent containing a plurality of micron size particles and comprising, by weight based on the total weight, from about 40 to 60% phenol in an aqueous buffer having a pH of from about 4 to 4.5 which is 2M in guanidinium thiocyanate or guanidinium chloride;

b. adding a water insoluble organic solvent to form a two phase mixture including the aqueous extraction solvent phase and an organic phase wherein the RNA is dissolved in the aqueous phase and the DNA and protein are concentrated in the organic phase or at the interface between the phases; and c. precipitating the RNA from the aqueous phase by the addition of a water soluble lower alkanol.

Still another object of the present invention is to provide a reagent useful for extracting RNA from a cellular source containing it together with DNA and protein which includes a mixture containing, by weight based on the total weight of the mixture, from about 40 to 60% phenol and from about 0.1 to 1% of a detergent in an aqueous buffer having a pH of from about 4 to 4.5.

Yet another object of the present invention to provide a method of isolating RNA from a cellular source containing it together with DNA and protein which includes the steps of:

a. mechanically releasing the RNA from a cellular source containing it in the presence of an extraction solvent containing a plurality of micron size particles and comprising by weight based on the total weight, from about 40 to 60% phenol and from about 0.1 to 1% detergent in an aqueous buffer having a pH of from about 4 to 4.5;

b. adding a water insoluble organic solvent to form a two phase mixture including the aqueous extraction solvent phase and an organic phase wherein the RNA is dissolved in the aqueous phase, the DNA and protein are concentrated in the organic phase or at the interface between the phases; and c. precipitating the RNA from the aqueous phase by the addition of a water soluble lower alkanol.

Another object of the present invention is to provide a container for isolation of ribonucleic acid (RNA) from RNA containing cells in a liquid medium which includes:

(i) a holder having therein, an RNA extractant solvent, a plurality of micron-size particles and at least one larger particle;

(ii) a cover assembly removably fastened onto the holder and having a cavity therein which is of sufficient volume to contain the liquid medium and the extraction solvent; and (iii) a friable sealing layer adapted to be broken by the larger particle upon reciprocal motion of the container, the sealing layer being adapted to separate the extractant solvent from the liquid medium until the sealing layer is broken by the larger particle.

An additional object of the present invention is to provide a container adapted to be firmly held in a reciprocal shaker useful for the extractive rupture of cells containing RNA to permit the extraction and recovery of the RNA therefrom, the container including:

(i) a holder containing an extraction solvent and a plurality of particles of a particle size suitable for fracturing the walls of the cells from which the RNA is to be extracted; and (ii) a cover assembly for closing the container during reciprocal motion to prevent leakage of the contents from the container, the volume of the extraction solvent being sufficient to dissolve substantially all of the RNA released as a result of the fracture of the cell walls.

Also an object of the present invention is to provide a container adapted to be firmly held in a reciprocal shaker and useful for the extractive rupture of cells containing RNA to permit the recovery of RNA therefrom, wherein the container includes:

(i) a holder containing an extraction solvent and a plurality of particles of a particle size suitable for fracturing the walls of the cells from which the RNA is to be extracted and at least one larger particle;

(ii) a cover assembly for closing the container thereby to prevent leakage of the contents from the container during reciprocal motion, the cover assembly having a cavity therein to contain the cellular source of RNA in a liquid medium; and (iii) a friable seal positioned between the extraction solvent and the liquid medium, which seal is adapted to be broken during reciprocal motion by the impact of the larger particle thereby to permit mixing of the contents of the container.

Application Ser. No. 08/227,514, entitled "Improved Method for Isolating RNA" describes and claims a method for extracting RNA from a natural source containing the RNA using reciprocal mechanical energy and micron size beads (particles) in an extraction solvent comprising phenol in an aqueous buffer at pH of from 4 to 4.5, which is 2 molar in guanidinium thiocyanate or guanidinium chloride.

The invention described in application Ser. No. 08/227, 516, now abandoned, entitled "Reagent and Process for Isolating RNA" is similar to the novel procedure of the previous application except for the use of a detergent in the buffered extraction solvent.

The process of this latter application has all of the advantages of the process of application Ser. No. 08/227, 514, now abandoned, and, in addition, utilizes an extractant which is much less expensive and more convenient to employ. Additionally, the process generally affords higher yields than the guanidinium process.

A common feature of both of the procedures of the two above-identified patent applications, in addition to the breaking of cell walls by mechanical energy from reciprocal motion, is the use of small solid micron-size beads (particles) to batter the cells and to break the cell walls like a bursting balloon. These particles are preferably glass beads, but may be any of a number of other particles such as metal, plastic or plastic coated metal particles.

The advantage of the process is that more cells are ruptured in a very short period of time so that more RNA is released to the extractant. In fact, the process can be completed in such a short period of time, just 30 seconds to 5 minutes, that no cooling is required, and no special steps need be taken to be certain that the reagents employed are RNAse free. RNAse is a contaminating enzyme that causes the RNA to degrade.

The present invention likewise features a procedure which makes possible the separation and isolation of RNA of exceptionally high purity in high yields. The procedure is very convenient and can be completed in a very short period of time, typically less than one half hour. The process is, moreover, applicable not only to biological tissue but also to microorganisms such as bacteria and also to plant cells as sources of RNA. Such sources, especially bacteria are much more convenient than biological tissue as a source of RNA because they are uniform, readily available in any desired quantities and easier to work with than biological tissue.

In another aspect, this invention relates to novel containers for conducting processes for isolation of RNA or other cellular components. The containers comprise a cover assembly and a lower member for containing the extractant and other components, hereinafter referred to as the "holder".

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

More particularly, the present invention relates to the application of sufficient mechanical energy to the cell walls of the selected RNA source in a particular extractant to disrupt the cell walls and release the RNA. The disruptive extraction process is effected in the presence of a chaotropic agent, i.e., a substance capable of disorganizing or disrupting molecular structures and molecular reactions within the cell.

The following are definitions of terms used throughout the present specification and claims:

The term "by weight", unless otherwise specified means by weight based on total weight.

"Reciprocal motion," "reciprocal energy," "reciprocal mechanical energy," "reciprocal agitation," "reciprocal shaking," and "reciprocally moving" are used interchangeably. These terms describe the use of a shaking motion, as opposed to rotational motion, in the presence of rapidly vibrating inert particles which are capable of fracturing the cell walls of prokaryotic organisms. The particles are preferably contained in a closed container, in a liquid medium. When the particles are "reciprocally agitated" in the presence of cells, two, opposing, colliding particles compress the cells in the middle and cause the cell walls to burst and release the cell components including RNA into the medium.

The term "liquid medium" can refer to a number of different media, including growth media, buffers or other liquids in which the cells are suspended.

The term "natural sources" means a source providing a biological sample of cells, including plant cells and tissues, eukaryotic cells and tissues, and prokaryotic cells.

The disruptive extraction process of the present invention is effected in the presence of, by weight, from about 40 to 60% phenol, in an aqueous buffer at a pH of from about 4 to 4.5 containing, as a chaotropic agent, sufficient guanidinium compound such as guanidinium thiocyanate or guanidinium chloride to provide a composition which is about 2 to 5 molar in the selected compound. Alternatively, the extractant may contain, by weight, 0.1-1% of a suitable surfactant. By disrupting the cells directly into an extraction medium, unstable cellular components such as RNA are immediately separated from proteins such as RNases, which would otherwise degrade the RNA.

In the process of the invention, cell walls of the RNA source, preferably bacteria are disrupted to release the RNA. Disruption is effected in an extraction solvent. The resulting mixture is then extracted with a water insoluble organic solvent. Since RNA is insoluble in organic solvents it remains in the aqueous phase. The DNA, proteins and other organic impurities either dissolve in the organic phase or collect at the interface between the layers. The separated RNA remains dissolved in the aqueous phase from which it may be precipitated by the addition of a water soluble lower alkanol such as methanol, ethanol or isopropanol. The thus isolated RNA may be recovered by filtration, centrifugation or other convenient procedure. The RNA, as recovered, is of exceptionally high purity and substantially free of DNA. The process is especially advantageous because of the high yields which can be obtained compared to other known processes.

Typically useful sources include *Staphylococcus aureus, Streptococcus pyogenes, Mycobacterium tuberculosis, Neisseria meningitidis, Saccharomyces cerevisiae* (yeast), and *Chlamydolomonas reinhardtii* (algae).

If desired, the DNA can be recovered in high yield and purity by conventional means well known to the skilled artisan.

Particularly important for the present invention is the discovery of the method of cell disruption in which the cell walls are fractured by force created by the reciprocal motion of the living cells and the cell wall fracturing particles in a closed container suspended in a liquid medium.

A novel reagent has now been discovered which is useful as an extraction solvent in this invention and makes possible the separation and isolation of RNA of exceptionally high purity in high yields by a very convenient procedure which can be completed in a very short period of time, typically less than one half hour.

The novel reagents of this invention are mixtures containing, by weight, from about 40 to 60% phenol and from about 0.1 to 1% surfactant and an aqueous buffer having a pH of from about 4 to 4.5. At this pH, phenol is insoluble in aqueous media. As a result, the mixture is a two phase mixture.

The process of the invention is applicable not only to biological tissue but also to microorganisms such as bacteria and also to plant cells as sources of RNA. Such sources, especially bacteria are much more convenient than biological tissue as a source of RNA because they are uniform, readily available in any desired quantities and easier to work with than biological tissue.

If desired, the DNA can be recovered in high yield and purity by conventional means well known to the skilled artisan.

There are a number of advantages to the process of this invention especially when conducted for the isolation of RNA. These include:

1. Applicability to RNA sources such as bacterial cells and plant cells which have heretofore been refractory to homogenization procedures with other phenol extractant media.
2. Recovery of RNA as a high yield product substantially uncontaminated by DNA.
3. Applicability to the production of both small and large quantities of RNA in batch or continuous processes.
4. Completion in a very short period of time which makes it possible to conduct the process without cooling without RNAse free reagents and without contamination by DNA fragments which would be produced by extended cell disruption procedures.
5. No ultracentrifugation is required.

6. The novel reagents of the invention are substantially odor free and readily available at commercially attractive prices.

The invention also relates to novel containers for conducting processes for isolation of RNA or other cellular components.

In the course of cellular growth, a large variety of different RNA is produced for conversion and expression of various proteins such as hormones, enzymes and other proteins. Following the expression of a required amount of such proteins, the cells would limit continued protein production by rapidly degrading the RNA coding for such protein. Accordingly, a maturing cell, at different stages of its growth or activity will contain differing amounts of the same RNA molecules or differing amounts of different RNA molecules.

It thus becomes important to extract the RNA from the living cell at different stages during the growth cycle of the cell to isolate and identify RNA species that may be short lived.

Certain of the embodiments of this invention are specially useful for these purposes. Thus, the cover assembly is adaptable to contain the growth medium, including all the necessary nutrients, for cell growth. Optionally, the cells can be grown separately and aliquots of the growth medium, including the cells, can be transferred to the cover assembly prior to rupture of the seal to permit mixing of the growth medium and cells with the extractive liquid. Alternatively, the cells can be isolated from a separate growth medium and added to the cover assembly in a buffer solution, with or without an additive to stop, or induce, the production of a selected protein. Optionally, the cells can be grown separately and aliquots of the growth medium, including growth cells, can be transferred to the cover assembly prior to rupture of the seal to effect mixing of the growth medium and the extraction liquid.

One embodiment of the container is especially useful for following the growth of cells by the isolation of various types of RNA produced in the course of cell development. In that embodiment, the cells of interest are cultured in a suitable medium in a cavity formed in the cover assembly or cultured separately and placed in the cavity. The cover assembly or the holder has a friable liquid-tight seal which separates the extractant and the liquid medium containing the cells. The holder contains, in addition to the extractant, a member of micron or sub-micron size particles and at least one large particle. When it is desired to extract the RNA the cover assembly is used to close the holder and the container is placed in a shaker. When the shaker is turned on, the resulting reciprocal motion of the large particle fractures the seal and allows the liquid medium and extractant to mix. The motion of the micron size particles bursts the cell walls and releases the cell components including RNA.

In another embodiment, the container comprises a holder which contains the extractant liquid, micron-sized beads and at least one larger bead in the extractant liquid, a friable seal, and a removable cover assembly. The cover assembly is removed, the cells in a liquid medium are placed on the friable seal and the cover closed. The container is reciprocally agitated, for example by shaking, so that the larger bead breaks the seal.

The container of the present invention allows for cell disruption by the application of mechanical energy to obtain highly purified RNA from natural sources containing it together with DNA and other contaminants, chiefly proteins. One important aspect of the mechanical energy involved in cell disruption in accordance with this invention is that it is reciprocally applied, preferably in the presence of micron or submicron size beads, or equivalent projectile like objects, so as to smash the cell walls in the manner of a bursting balloon. Rotational energy such as generated with a blender or other homogenizer is not useful because the cells simply rotate and do not collide efficiently with each other and with the beads to allow the cells to be crushed between the beads.

The extraction solvent used is the guanidinium salt containing liquid described above.

Any of a wide variety of well known buffers which will permit control of the pH within the selected range may be employed. Buffers based on sodium acetate or sodium citrate are presently preferred because they are readily available and provide excellent results. Other buffers known to the skilled artisan may be used.

The extraction reagent containing the guanidine type chaotropic agent may optionally contain an antioxidant to limit the spontaneous oxidation of phenol and increase the shelf life of the extraction reagent. Typically useful antioxidants include organic antioxidants such as 2-mercaptoethanol, dithiothreitol, 2-hydroxy quinoline and cysteine.

The first step in the practice of this invention is to mechanically fracture the cell walls of the cellular RNA source such as bacteria, the eukaryotic cells of biological tissue or plant cells. This may be accomplished with any of a variety of available instruments of which presently preferred are bead beaters such as the Mini Bead Beater available from BioSpec Products of Bartlesville, Okla. Other instruments are available.

Bead beaters are preferred instruments for treating the RNA source. Typically, the size of the bead is from about 0.1 to 1.0 microns, and will vary with the size of the DNA carrier cells. Even more preferable is the use of the FastPrep™ machine made by Savant Instruments (Farmingdale, N.Y.) because of its fast speed, reducing the time needed for complete disruption.

One of the most important features of the selected shaker is that it is capable of generating enough mechanical energy by reciprocal motion to break the cell walls of bacterial cells and release the RNA. This may be accomplished by rapidly vibrating glass beads or other inert particles in the extraction reagent in the presence of the bacteria or other RNA source. Such beads are commercially available in a variety of sizes from several sources. They can be shaken at selected speeds to provide sufficient mechanical energy to disrupt the cell walls.

RNA release is effected with the bacterial cells or other RNA source suspended in the extraction solvent. The time required depends principally upon the size of the source from which the RNA is being extracted since the cell size of various RNA sources such as bacteria, yeasts and plant cells varies appreciably. For small batches of bacteria or other source, 30 seconds may be adequate. For larger batches two or three minutes may occasionally be required. Time is a critical factor because the half-life of some of the RNA species is very short (1–2 minutes).

At the end of the disruption step when most of the RNA has been released into the buffered solvent, the solvent is extracted with an organic solvent which is substantially water insoluble. The solvent is added at the end of the extraction procedure. Typically useful solvents include substituted and unsubstituted lower hydrocarbons such as chloroform.

During the extraction process the DNA dissolves in the organic solvent and may be recovered by standard techniques known to the skilled artisan. The RNA remains dissolved in the aqueous buffer and may be precipitated with isopropanol as described above and illustrated in the example.

The present invention is especially useful when practiced with the novel reagent referred to above. The reagent is a two phase mixture containing selected amounts of phenol and at least one detergent in an aqueous buffer at a pH of about 4. This pH is selected because when the hydrogen ion concentration is at this level, RNA is soluble in water and DNA is insoluble. A preferred reagent is the FastRNA™ reagent manufactured by Bio 101.

The selected detergent may be any of a variety of conventional surfactants including anionic, cationic, non-ionic and amphoteric surfactants.

Typically useful anionic detergents include, for example, sodium lauryl sulfate, sodium-n-decyl sulfate and triethanolamine dodecyl benzene sulfonate.

Cationic detergents useful in the practice of the invention include, by way of example, cetyl trimethyl ammonium bromide and other N-alkyl quaternary ammonium halides, as well as polyethoxylated quaternary ammonium chloride.

Amongst the nonionic detergents, there are tallow fatty alcohol ethoxylates, ethoxylated tridecyl alcohol, ethoxylated tridecanol, nonyl phenol ethoxylate and octylphenoxy polyethoxy ethanol.

Amphoteric detergents include, for example cocoamidopropyl betaine, disodium tallowimino dipriopionate and cocoamido betaine.

The surfactant which is presently the most preferred is cetyl trimethyl ammonium bromide because it gives the best yields of DNA free product.

All of these detergents, and many other equivalent surfactant compounds are readily available from commercial sources.

As with the previous procedure, as of a number of buffers or optional antioxidants may be employed.

The process of the invention when conducted with the novel extraction solvent is substantially similar to the process described above with the guanidinium salt.

Figure 1:
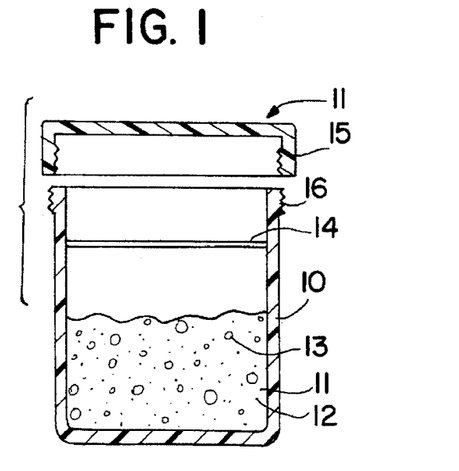
FIG. 1 is a side cross-sectional view of one embodiment of the present invention showing a container comprising a holder and its cover.

As shown in FIG. 1, the novel container which is especially useful when employed in accordance with the invention to isolate RNA or other cellular components comprises a holder 10 and a cover assembly 11, both preferably of glass or an inert plastic. The holder contains a liquid RNA extractant 11, such as those described above.

The holder 10 has preferably a cylindrical side wall so that it is round in sections perpendicular to FIG. 1 and, like all embodiments of this invention, is adapted to be firmly held in a reciprocal shaker. A large number of micron-size particles, suitably beads 12 are within the liquid extractant. Preferably the beads are of glass or metal and preferably they are from about 0.1–1.0 mm in diameter.

Any convenient number or weight of such beads may be employed.

For research purposes, which normally require only small amounts of RNA the container may be very small. Typically, the total volume is from about 1.5–2.5 ml. Larger containers may be employed to obtain greater quantities of RNA.

The holder is sealed with a friable seal 14 which may be of the same material as the holder itself and typically, is positioned about one-half way up the holder wall. The seal 14 is liquid-proof and yet light enough so that it may be broken by the weight of the particles reciprocally moving in the container or, preferably by a larger particle such as bead 13. The larger bead may be of any convenient size and weight to fracture the seal.

The cover assembly 11 has internal screw threads 15 which mate with the external screw threads 16 of container 10.

Figure 2:
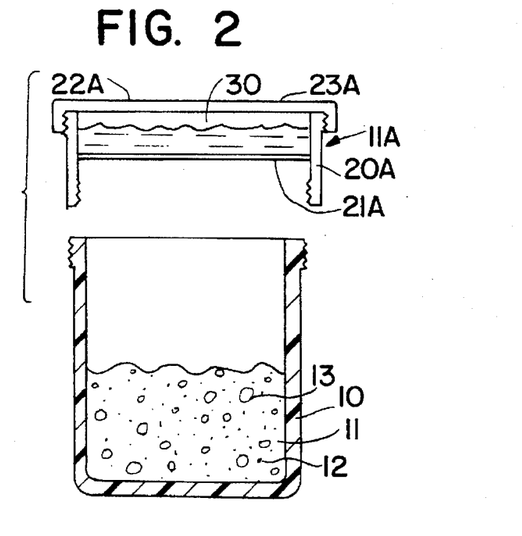
FIGS. 2–4 are side cross-sectional views of other embodiments of the containers of the present invention.
Figure 3:
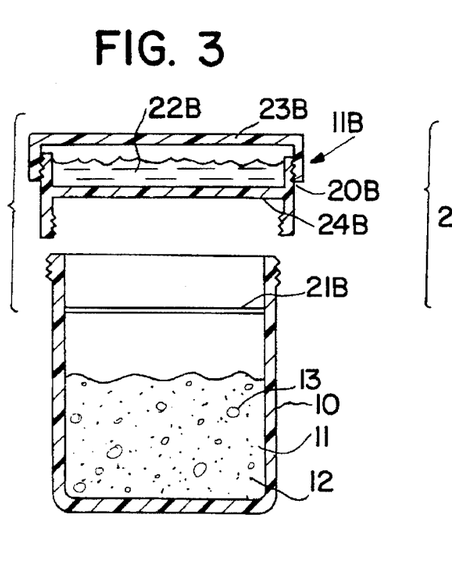
Figure 4:
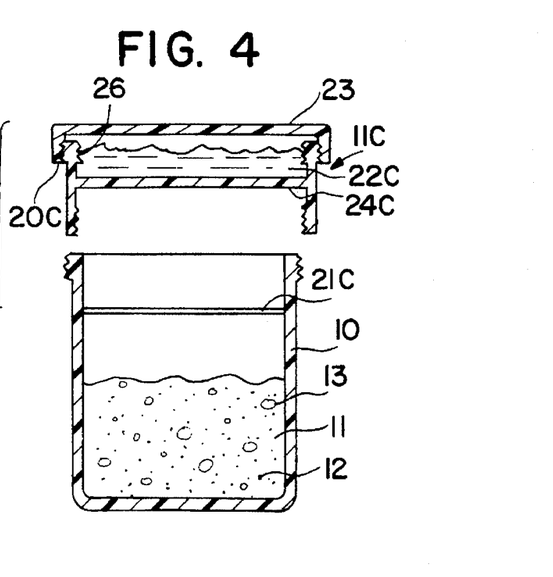

In the second, third and fourth embodiments shown in FIGS. 2–4, the holder 10, the extractant liquid 11, small-size beads 12 and larger bead 13, about 3–5 mm in diameter, are the same as in the first embodiment, shown in FIG. 1. In addition, the process steps used to isolate the RNA from the extractant liquid will also be the same.

In the second embodiment shown in FIG. 2, the cover assembly 11A acts to store and nurture the cells. The cover assembly 11A has a ring-like side wall body member 20A, a friable liquid tight layer 21A which acts as the bottom wall of the cavity 30, the cells of interest in a suitable medium 22A and a removable top cover 23A. The container consists of the holder 10, with its beads and extractant liquid, and the cover assembly 11A which is screwed, or otherwise fastened, onto the container body.

In use, when the user desires to isolate RNA from the cells in medium 22A, the cover assembly 11A will be screwed to holder 10 and with top cover 23A in place the container vigorously shaken for about 30 seconds to 5 minutes causing the large bead 13 to break the friable layer 21A and the culture medium 22A or other liquid medium containing the cells will mix with the extractant liquid 11 and the other components in the holder.

In the embodiment of FIG. 3, the cover assembly 11A has the cells of interest in liquid medium 22B. The cover assembly has a ring-like sidewall 20B, cells of interest in a medium 22B, a solid top removable lid 23B and a solid bottom wall 24B. The container 10 has a friable liquid tight layer 21B, as in the first embodiment.

In operation, the user will unscrew cover assembly 11B from container 10, unscrew the top lid 23B and pour the medium 22B into the container 10, or transfer it by pipette, where it will be held on top of the friable layer 21B. The cover assembly 11B is then replaced on the holder and the container shaken so that the bead 13 breaks the friable layer 21B, all of the components mix and the cell walls ruptured by the action of the beads, thereby to release the RNA.

In the fourth embodiment, shown in FIG. 4, the cover assembly 11C has a ring-like side wall 20C, cells of interest in a culture or other medium 22C, a solid bottom wall 24C, and a solid top lid 23C and a top rim 25 having internal screw threads 26. The holder 10 has a friable liquid-tight layer 21C.

In operation, the user will remove cover assembly 11C from holder 10, unscrew the top lid 23C, and screw the cover assembly onto holder 10 with the screw threads 26. The container will then be shaken so that the bead 13 breaks the friable layer 21C.

As indicated above, the total volume of the container should be sufficient so that when it is closed, it will hold the extraction solvent, the liquid medium and the other components under conditions so that the entire mixture can be conveniently and efficiently shaken. A general rule for this purpose is that the total volume of the closed tube is one third occupied by beads, one third reagent/cells and ⅓ air space.

For use in research or other laboratories where relatively small amounts of RNA is required, the containers can be packaged in kits containing one or a plurality of containers together with a container of organic solvents and other accoutrements appropriate to the practice of the process. The kits may include a selection of containers with small beads of different sizes to accommodate the varying sizes of the cells employed as the RNA source. Such containers are especially useful with shakers which can hold a plurality of container, even up to 20 or more. Such machines and containers are especially useful when it is desired to conduct a number of RNA isolations simultaneously or sequentially.

The containers of this invention have been described principally with reference to four specific embodiments and to the isolation of RNA using an extraction solvent containing either a detergent or guanidium salt as the chaotropic agent used to disrupt the molecular structure and molecular interactions in the cell containing the RNA to be isolated. Other chaotropic agents can be employed.

It will be apparent to the skilled artisan that the concept of the containers can be practiced utilizing other structures that are equivalent to the structures illustrated and described. For example, the friable sealing layer could be fixed at the top of the holder so that it breaks when the cover assembly is tightly screwed into place thereby eliminating the need for large beads. The same result could be achieved by sealing a pointed member on the inside of the cover assembly dimensioned so that it will fracture the sealing layer when the cover assembly is screwed tightly into place.

Of course, the cover assembly can be fixed to the holder by means which are equivalent to the threads shown, for example by a force fit.

Since rupture of the cell walls releases all of the cellular substituents, this invention can be used with or without chaotropic agents and extraction solvents such as those described above to isolate other cellular components using known isolation procedures. For example, proteins may be isolated from a disrupted mixture containing an extraction solvent that comprises a neutral buffer and a cocktail of protease inhibitors.

As another example, the processes and containers of the invention may be used to efficiently and rapidly shred tissue such as skin, intestine, gastric, liver etc. into the component parts for the isolation of certain components. Individual cellular components, e.g., enzymes, may then be isolated using standard chromatographic techniques. Similarly, structural components e.g., connective tissue, membranes, cell wall components, etc. may be separated by differential centrifugation techniques.

The following examples are given by way of illustration only and should not be considered limitations of this invention, many apparent variations of which are possible without departing from the spirit or scope thereof.

EXAMPLES 1–6

RNA and DNA were isolated from the following microorganisms using the protocol described below:

1. *Staphylococcus aureus*
2. *Streptococcus pyogenes*
3. *Mycobacterium tuberculosis*
4. *Neisseria meningitidis*
5. *Saccharomyces cerevisiae* (yeast)
6. *Chamydolomonas reinhardtii* (algae)

Steps

1. Centrifuge 10 ml of cells to be processed ($\sim$1–5$\times$10$^8$ per ml).
2. Aspirate and discard the culture supernatant.
3. Resuspend bacterial pellet in 1 ml of extraction reagent. Prepare 5 ml of the extractions by adding:

| | |
|---|---|
| Phenol | 2 ml (40%) |
| 10% CTAB* | 0.5 ml (1%) |
| 2M NaAc pH 4 | 125 µl (50 mM) |
| 1M DTT | 5 µl (1 mM) |
| water | 2.37 ml |

*cetyl trimethyl ammonium bromide

This results in a two-phase reagent which needs to be vortexed vigorously before pipetting 1 ml of the reagent into the tube.

4. Transfer the reagent mixture into sterile microfuge tube containing$\approx$0.5 ml (1.65 gm) of 0.1 mm glass/Zirconia beads (larger beads used for yeast and algae).
5. Shake at 6000 rpm for 20 seconds with reciprocal motion. Pulse spin to settle the glass/Zirconia beads to the bottom of the tube.
6. Add 200 µl of chloroform. Let sit for 2 min.
7. Vortex for 25 seconds.
8. Centrifuge for 12,000 g for 15 min at 4° C.
9. Aspirate the upper aqueous phase.
10. Add 0.5 ml of isopropanol. Incubate for 10 min.
11. Spin 12,000 g for 10 min at 4° C.
12. Wash pellet with 70% ethanol and spin for 5 min at 5000$\times$g.
13. Discard the 70% ethanol wash and air dry for 5–10 min.
14. Resuspend RNA for storage in 100 µl of either diethyl pyrocarbonate treated water or 0.5% sodium dodecyl sulfate.
15. To obtain DNA, the interphase containing the DNA is re-extracted twice with phenol/chloroform (50/50 v). The upper aqueous phase is saved. One-tenth volume of sodium acetate (3M pH 5.2) is added. The DNA is precipitated with 3 volumes of 100% ethanol, centrifuged, washed with 70% ethanol and recentrifuged. The pellet containing DNA is resuspended in Tris EDTA buffer and used for restriction digestion or cloning.

EXAMPLE 7

Figure 5:
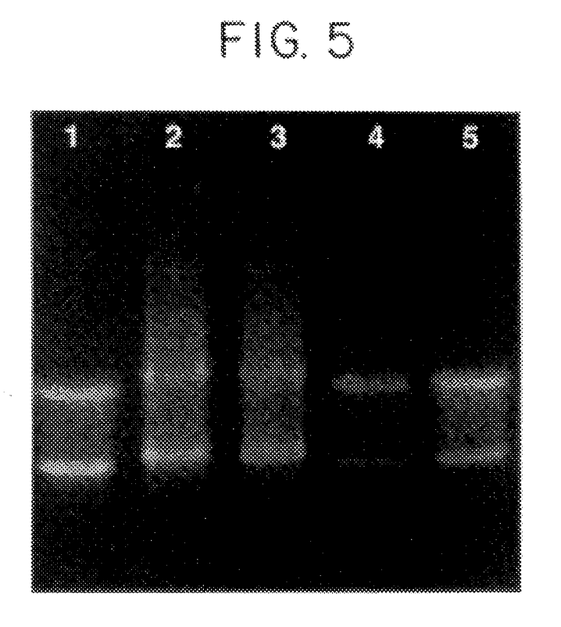
FIG. 5 shows RNA purified from various mouse tissues using the FastPrep™ System, run on a native 1.2% agarose gel and stained with EtBr. Lane 1: liver; Lane 2: kidney; Lane 3: brain; Lane 4: spleen; Lane 5: muscle. Only the 18S and 28S rRNA bands are shown.
Figure 6:
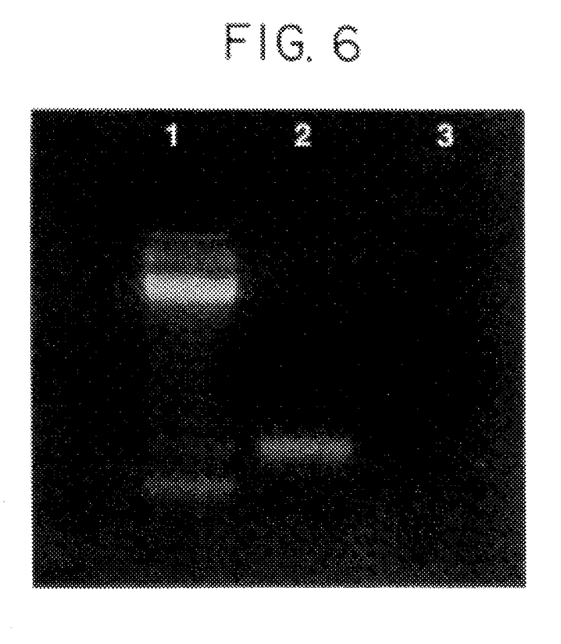
FIG. 6 shows the results of RT-PCR on mouse liver RNA using B-actin primers. Samples were treated with DNaseI prior to amplification. Lane 1: 123 bp ladder; Lane 2: reverse transcription and amplification; Lane 3: amplification in the absence of reverse transcription.

Fresh chunks of mouse liver, kidney, brain, spleen and skeletal muscle (~50 mg each) are placed in 2 ml tubes containing chaotropic RNA stabilizing reagents and a lysing matrix and immediately processed in the FastPrep™ System for 30–60 seconds (There is no need for pre-homogenization). Following centrifugation, the clear RNA containing supernatant is ethanol precipitated, or matrix purified and eluted in 100 µl DEPC $H_2O$. 10–20 µl are run on a native agarose gel (FIG. 5). FIG. 6 shows an RT-PCR analysis of liver RNA.

TABLE 1

| TYPICAL RNA YIELD FROM VARIOUS SOURCES | | |
|---|---|---|
| SAMPLE | AMOUNT | TOTAL RNA YIELD |
| Muscle Tissue | 100 mg | 100–150 µg |
| Liver Tissue | 100 mg | Up to 800 µg |
| Fibroblasts | 10$^7$ Cells | 50–80 µg |
| Lymphocytes | 10$^7$ Cells | 70–100 µg |
| Young Plant Leaf | 250 mg | 50–200 µg |
| Mature Plant Leaf | 250 mg | 25–150 µg |
| Bacterial Cells | 10$^9$ Cells | 50–100 µg |
| Yeast Cells | 10$^9$ Cells | 50–100 µg |

EXAMPLE 8

A method for isolating RNA from gram positive bacteria which is fast, simple and requires no expensive equipment utilized the FastRNA™ (BIO 101, Vista, Calif.) kit together with the FastPrep™ machine (Savant). The method was used for *Staphylococcus aureus* and *Saccharomyces cerevisiae* from which RNA extraction had previously been known to be difficult.

For this procedure, bacteria were cultured in growth media overnight, diluted 1:100 in 10 mls of fresh media, and grown to mid log, late log and post-exponential phases corresponding to $OD_{650\ nm}$ of 0.7, 1.1 and 1.7, respectively. The bacteria were then pelleted (2,500$\times$g for 10 minutes at 4° C.) and resuspended in 1 ml of reagent. The cells were transferred to a 2 ml microfuge tube, to which 500 μl of Zirconia/Silica beads (0.1 mm size) were added.

The tube was shaken in Savant machine for 20 seconds at 6500 rpm then placed on ice. 200 μl of chloroform was added to the tube. After vortexing for 15 seconds and incubating at RT for 2 minutes, the mixture was centrifuged at 12,000×g for 15 minutes at 4° C. The RNA was harvested from the aqueous phase (top layer), precipitated with 0.5 ml of isopropanol and pelleted (12,000×g for 10 minutes at 4° C.). The pellet was washed with 75% ethanol, air-dried and resuspended in 100 μl of 0.5% SDS in DEPC-treated water. The RNA concentration was determined spectrophotometrically.

Figure 7:
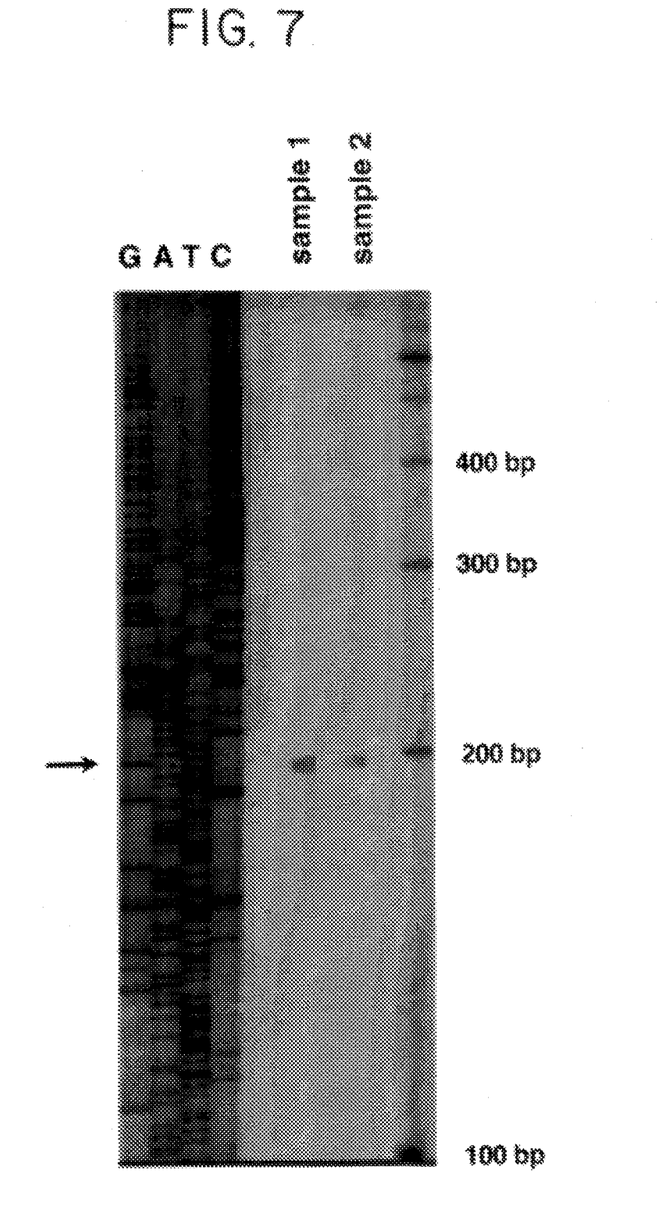
FIG. 7 shows the primer extension of the sara transcript of *S. aureus*. RNA was purified using FastRNA™ reagent and FastPrep™ machine. The RNA was annealed to $^{32}P$ radiolabeled oligonucleotide primer and extended with reverse transcriptase, thereby yielding a primer extension product. By running a sequencing reaction with a DNA template (labeled GATC) and an identical primer, the transcription start site of the sara transcript was mapped to position 101 in a sarA clone (see arrow). The samples 1 and 2 represent two different RNA preparations with the same method.
Figure 8:
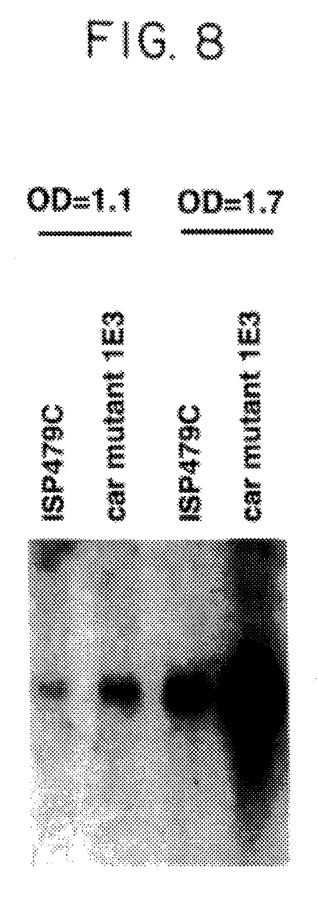
FIG. 8 is a Northern blot of α-hemolysin transcript of parental strain ISP479C and car mutant 1E3. The size of the transcript was≈1.8 kb. The $OD_{650}$ of 1.1 and 1.7 correspond to late-exponential and post-exponential phases, respectively.
Figure 9:
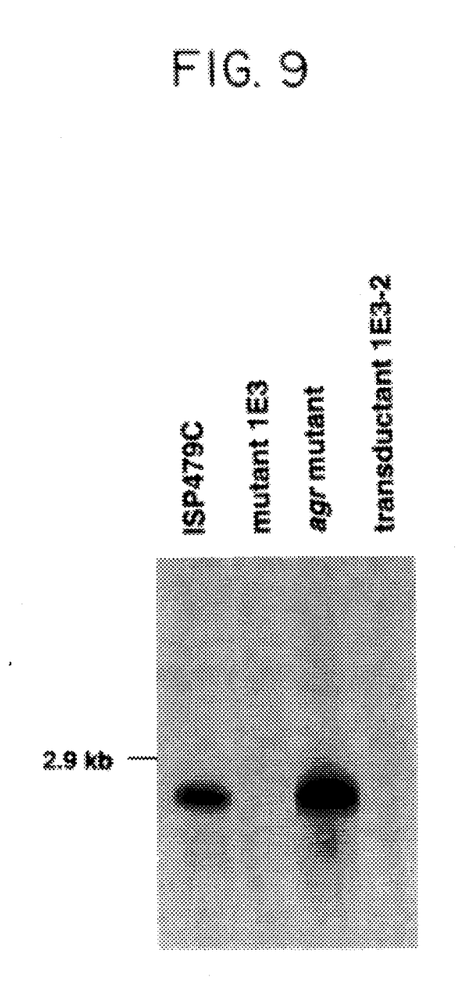
FIG. 9 is a Northern blot of protein A transcript in parent ISP479C, car mutant 1E3 and transductant 1E3-2. The agr mutant of ISP479C, strain B2, is included as a positive control. The protein A transcript is≈1.9 kb. The arrow points to the 23S ribosomal RNA band which serves as a RNA marker.

Five μg of each sample was electrophoresed through a 1.5% agarose 0.66M formaldehyde gel in MOPS running buffer (20 mM MOPS, 10 mM sodium acetate, 2 mM EDTA, pH 7.0). With this method, we were able to obtain a high yield of RNA with good purity as evidenced by the $A_{260}/A_{280}$ ratio (Table 1). This method of extraction is also highly efficient as the RNA yield appeared to be proportional to the number of bacterial cells (Table 1). The integrity of RNA species was also confirmed in formaldehyde gels (FIG. 7).

Primer extension was carried out with 30 μg of RNA resuspended in DEPC-treated water. The RNA was precipitated in the presence of the primer which was end-labeled ($5×10^4$ cpm) and then prehybridized overnight at 30° C. The reaction mixture was then precipitated with 5 volumes of ethanol in the presence of 10% acetic acid, washed and dried. Reverse transcription was carried out, and the reaction incubated at 42° C. for 90 minutes, heated at 65° C. for 0 minutes and then incubated with 1 μl of RNase A for 15 minutes at 55° C. The reaction was cleaned up with QIAquick nucleotide removal kit (Qiagen), ethanol precipitated, dried and resuspended in 10 μl of TE and 10 μl of Sequenase stop solution. The reaction was heated to 95° C. for 5 minutes, chilled on ice and loaded on sequencing gel.

EXAMPLE 9

Staphylococcal RNA was extracted from a 10 ml culture grown to late log or postexponential phase in CYGP was pelleted, resuspended in 1 ml of FastRNA™ reagent (BIO 101) and 0.5 ml of 0.1 mm Zirconia/Silica beads and shaken at 6,000 rpm in a high speed reciprocating homogenizer (FastPrep™ machine, Savant Instruments) for 20 seconds. [This apparatus is the subject of copending U.S. patent application Ser. No. 08/294,544.] After adding 200 μl of chloroform, the mixture was centrifuged at 12,000 g for 10 minutes. The RNA in the upper aqueous layer was precipitated with isopropanol and resuspended in DEPC-treated water. The total cellular RNA yield was≈0.5–1 mg with an $A_{260}/A_{280}$ ratio of 2.0. The integrity of the RNA species was verified with a formaldehyde gel.

Five μg of RNA from each bacterial strain was applied to a 1.5% agarose-0.66M formaldehyde gel in MOPS running buffer as described in Cheung et al ((1994) *J. Bacteriol.* 176:580–585). RNA was transferred to Nytran nylon membrane using the Turboblotter System (Schleicher & Schuell, Keene, N.H.). RNA on the membrane was cross-linked with UV light, hybridized with a $^{32}P$ labeled gel-purified protein A or α-hemolysin probe in 50% formamide at 42° C. overnight, washed and autoradiographed as described in Cheung et al (1994).

What is claimed is:

1. A method of isolating DNA from a cellular source containing it together with RNA and protein comprising the steps of:

a. mechanically releasing cellular components from a cellular source containing it by the application of reciprocal energy in the presence of an extraction solvent containing a plurality of micron size particles and comprising, by weight based on the total weight, from about 40 to 60% phenol in an aqueous buffer having a pH of from about 4 to 4.5 which is 2M in guanidinium thiocyanate or guanidinium chloride;

b. adding a water insoluble organic solvent to form a two phase mixture comprising an aqueous extraction solvent phase and an organic phase wherein the RNA is dissolved in the aqueous phase and the DNA and protein are concentrated in the organic phase or at the interface between the phases;

c. extracting the interphase with phenol and chloroform; and d. precipitating the DNA with ethanol.

2. A method of isolating a cellular component which comprises mechanically releasing the component by the application of reciprocal mechanical energy to a suspension of cells in a liquid medium in a container which also contains a plurality of micron-size particles thereby to fracture the cell walls and release the cell component into the liquid medium and isolating said cellular component from the medium.

3. The method of claim 2 wherein the liquid medium additionally contains a chaotropic agent.

4. A method of isolating RNA from a cellular source containing it together with DNA and protein which comprises the steps of:

a. mechanically releasing the RNA from a cellular source containing it by the application of reciprocal energy in the presence of an extraction solvent containing a plurality of micron size particles and comprising, by weight based on the total weight, from about 40 to 60% phenol in an aqueous buffer having a pH of from about 4 to 4.5 which is 2M in guanidinium thiocyanate or guanidinium chloride;

b. adding a water insoluble organic solvent to form a two phase mixture comprising the aqueous extraction solvent phase and an organic phase wherein the RNA is dissolved in the aqueous phase and the DNA and protein are concentrated in the organic phase or at the interface between the phases; and c. precipitating the RNA from the aqueous phase by the addition of a water soluble lower alkanol.

5. The method of claim 4 including the further step of recovering the RNA by separating it from the aqueous phase from which it has been precipitated by filtration or by centrifugation and removal of the supernatant aqueous phase.

6. The method claim 2 wherein the extraction is conducted in the presence of detergent or mixtures thereof.

7. A method of isolating RNA from a cellular source containing it together with DNA and protein which comprises the steps of:

a. mechanically releasing the RNA from a cellular source containing it in the presence of an extraction solvent containing a plurality of micron size particles and comprising by weight based on the total weight, from about 40 to 60% phenol and from about 0.1 to 1% detergent in an aqueous buffer having a pH of from about 4 to 4.5;

b. adding a water insoluble organic solvent to form a two phase mixture comprising an aqueous extraction solvent phase and an organic phase wherein the RNA is dissolved in the aqueous phase, the DNA and protein are concentrated in the organic phase or at the interface between the phases; and c. precipitating the RNA from the aqueous phase by the addition of a water soluble lower alkanol.

8. The method of claim 7 including the further step of recovering the RNA by separating it from the aqueous phase from which it has been precipitated by filtration or by centrifugation and removal of the supernatant aqueous phase.

9. The method of claim 7 wherein the detergent is cationic.

10. The method of claim 9 wherein the detergent is cetyl trimethyl ammonium bromide.

* * * * *